(12) United States Patent
Massengale (10) Patent No.: US 10,485,677 B2
(45) Date of Patent: Nov. 26, 2019

(54) LUMBAR FUSION

(71) Applicant: Justin Massengale, Brookline, MA (US)

(72) Inventor: Justin Massengale, Brookline, MA (US)

(73) Assignee: Justin Massengale, Brookline, MA (US)

( * ) Notice: Subject to any disclaimer, the term of this patent is extended or adjusted under 35 U.S.C. 154(b) by 0 days.

(21) Appl. No.: 15/581,291

(22) Filed: Apr. 28, 2017

(65) Prior Publication Data

US 2018/0000611 A1     Jan. 4, 2018

Related U.S. Application Data

(60) Provisional application No. 62/328,747, filed on Apr. 28, 2016.

(51) Int. Cl.
| | |
|---|---|
| *A61B 17/02* | (2006.01) |
| *A61F 2/44* | (2006.01) |
| *A61F 2/46* | (2006.01) |

(52) U.S. Cl.
CPC .......... *A61F 2/4611* (2013.01); *A61F 2/4455* (2013.01); *A61B 17/0206* (2013.01); *A61B 2017/0256* (2013.01); *A61F 2002/4475* (2013.01); *A61F 2002/4635* (2013.01); *A61F 2002/4681* (2013.01)

(58) Field of Classification Search
CPC .................. A61F 2/4611; A61F 2/4455; A61F 2002/4475; A61F 2002/4635; A61F 2002/4681; A61B 17/0206; A61B 2017/0256

USPC ....... 623/17.11–17.16; 606/86 A, 90, 96, 99, 606/246–289

See application file for complete search history.

(56) References Cited

U.S. PATENT DOCUMENTS

| | | | |
|---|---|---|---|
| 2007/0270951 A1* | 11/2007 | Davis | A61F 2/4455 623/17.11 |
| 2011/0184465 A1* | 7/2011 | Boehm | A61B 17/7005 606/264 |
| 2013/0289354 A1* | 10/2013 | Ainsworth | A61B 17/0642 600/204 |
| 2013/0289654 A1* | 10/2013 | Zhang | A61N 1/36032 607/57 |
| 2015/0080973 A1* | 3/2015 | Eastlack | A61F 2/4455 606/86 A |
| 2016/0287236 A1* | 10/2016 | Garcia-Bengochea | A61B 17/0206 |
| 2017/0238984 A1* | 8/2017 | Kleiner | A61F 2/447 |

* cited by examiner

*Primary Examiner* — Pedro Philogene
(74) *Attorney, Agent, or Firm* — Adler Pollock & Sheehan P.C (57) ABSTRACT

Apparatus and methods for lumbar fusion. An apparatus includes a large footprint interbody cage, a two bladed mini-open retractor, and a pole, the large footprint interbody cage laid into a concavity forward by outwardly bent tines of the two bladed mini-open retractor, the pole for impacting the large footprint interbody cage into an interbody space advanced through a stab incision separate from a main incision and attached to the large footprint interbody cage.

2 Claims, 10 Drawing Sheets

LUMBAR FUSION

CROSS REFERENCE TO RELATED APPLICATIONS

This application claims priority under 35 USC § 119(e) to U.S. Provisional Application Ser. No. 62/328,747, filed on Apr. 28, 2016, and entitled LUMBAR FUSION DEVICE AND METHOD, the entire contents of which are hereby incorporated by reference.

BACKGROUND OF THE INVENTION

The present invention relates generally to treating a variety of spinal disorders, and more particularly to lumbar fusion.

Degenerative disc and facet joint disease of the lumbar spine is common in the aging population, and is one of the most frequent causes of disability. Lumbar spondylosis may result in mechanical back pain, radicular and claudicant symptoms, reduced mobility and poor quality of life. Surgical interbody fusion of degenerative levels is an effective treatment option to stabilize the painful motion segment, and may provide indirect decompression of the neural elements, restore lordosis and correct deformity. The surgical options for interbody fusion of the lumbar spine include: posterior lumbar interbody fusion (PLIF), transforaminal lumbar interbody fusion (TLIF), minimally invasive transforaminal lumbar interbody fusion (MI-TLIF), oblique lumbar interbody fusion/anterior to psoas (OLIF/ATP), lateral lumbar interbody fusion (LLIF) and anterior lumbar interbody fusion (ALIF).

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates generally to treating a variety of spinal disorders, and more particularly to lumbar fusion.

In an aspect, the invention features a system including a large footprint interbody cage, a two bladed mini-open retractor, and a pole, the large footprint interbody cage laid into a concavity forward by outwardly bent tines of the two bladed mini-open retractor, the pole for impacting the large footprint interbody cage into an interbody space advanced through a stab incision separate from a main incision and attached to the large footprint interbody cage.

In another aspect, the invention features a system including an access tube internal trochar, a slotted access tube, a curved track, and a spatula-style muscle spreading instrument, the trochar, access tube, curved track and spreading instrument used for an implant for interbody fusion, including disc space and endplate preparation.

In another aspect, the invention features a method including advancing a tunnel with a trochar inside through an incision in the skin and underlying facsia to dock on a lumbar facet through an off-midline incision, performing an ipsilateral facetectomy, preparing a disc space with an internal serial passage of instruments down a visualization tunnel, adjusting an angle of the tunnel, packing a cage with arthrodesos material, attaching the cage to an inserter instrument, adjusting an angle of the tunnel to enable insertion of the cage in as diagonal an orientation as possible into an interspace through the tunnel, and disconnecting the introducer from the cage.

In still another aspect, the invention features a method including performing an ipsilateral facetectomy and disc annulotomy, introducing disc preparation instruments, advancing each sequentially beneath skin muscle and soft tissue, guiding each instrument through a slot in a convex lateral retractor blade, visualizing each instrument emerging into a surgical field, guiding each instrument into the previously created ipsilateral disc annulotomy, advancing each instrument to a final position across a midline in a contralateral pedicular zone of an interspace, and packing a cage and laying the packed cage into initial insertion position in an ipsilateral foramen over an annulotomy.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein.

DETAILED DESCRIPTION

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "or" is intended to mean an inclusive "or" rather than an exclusive "or." That is, unless specified otherwise, or clear from context, "X employs A or B" is intended to mean any of the natural inclusive permutations. That is, if X employs A, X employs B, or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

For adult degenerative spine diseases, such as osteoarthritis, stenosis, and spondylolisthesis causing mechanical back pain and neurological symptoms, lumbar fusion is typically performed for two purposes:

(1) To immobilize the micromotion using screw fixation at the joint suspected of acting as a pain generator, and (2) To achieve additional restoration of lordosis (spinal angle), correction of coronal deformity (scoliosis), and indirect neural foraminal decompression (alleviation of nerve impingement) by using an intervertebral, or interbody, implant.

It has been shown that interbody implants with larger footprint surface area for contacting the vertebral endplates, particularly the apophyseal ring area of the outer verbetral border which is structurally stronger than than the endplate's central portion, can more effectively maintain durable improvement in both of those parameters, compared to smaller implants which durably improve either lordosis or neural foraminal height but less often both, which leaves patients with either suboptimal benefit or higher risk of needing more surgery later.

In general, fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders.

Various approaches for the insertion of interbody cages are commonly divided into two categories:

(1) Posterior approach, in which the access corridor for the installation of the implant is directed at the posterior part of the vertebral column and which can therefore be achieved with the same surgical patient position as needed for the screw fixation, and (2) Approaches directed at the anterior or lateral aspects of the vertebral column, with requires a separate incision and usually also a separate patient positioning step to place the interbody implant in addition to that needed to place the fixation screws.

Clinical decision making in the selection of a surgical strategy represents a risk and benefit tradeoff balance. On one hand, the anterior incision and exposure portion of the combined two stage operation comes with additional risks of operative morbidity and nerve injury associated with the extra dissection. On the other, because of different anatomical restrictions of working around spinal canal from the posterior approach, the cages available for placement from the anterior approach have larger footprints than those designed to be placed from the posterior approach, and it is generally perceived that the posterior approach cannot accommodate the same large footprint style cages that can be placed anteriorly, due to these anatomic factors. Cages with in situ mechanical expandability have been designed and marketed to circumvent this limitation, but mechanical components are prone to fracture and failure. Also, because the correction of advanced degenerative deformities can require substantial impaction force which is most effective when achieved at the time of initial cage insertion, cages with a small insertion footprint cannot distribute the force over the apophyseal ring area of the vertebral endplate during that initial impaction as well as a cage with a large starting footprint could. The need for such concentrated impact force could compromise the expandable cage's long term effectiveness, via potential damage to the vertebral endplates during impaction, predisposing the cage to subsidence into the damaged endplates over time, and resulting in relapse of the anatomical deformity that the implant is intended to help correct.

Regardless of the approach, the typical procedure for inserting a common threaded and impacted fusion cage is the same. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space.

The present invention provides a cage comparable in size to that currently available for anterior approaches, but implantable through the posterior approach, which achieves all the goals of anatomical and biomechanical advantages of the large cage in deformity correction and foraminal expansion while circumventing the need for the additional position, incision and dissection steps which a two-stage combined anterior and posterior operation requires.

More specifically, the present invention provides a large-footprint non-expandable cage spacer suitable for implantation through a posterior-only transforaminal approach, and a method for its installation, along with instruments for the preparation of the endplates to debride the bony surface of cartilage and soft tissue and create a sufficiently capacious space to accommodate this large implant.

Figure 1:
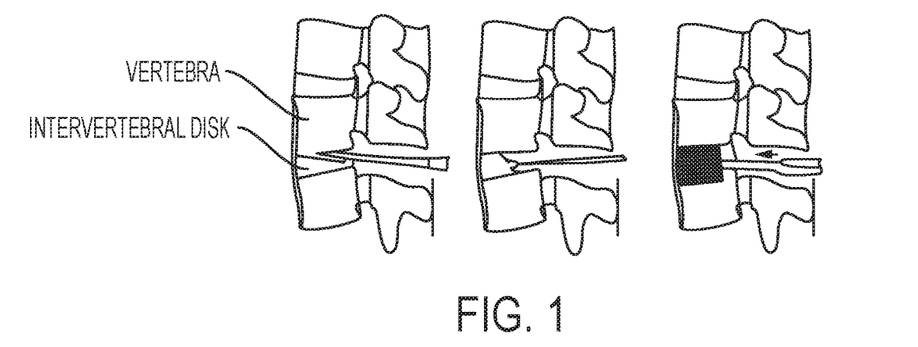
FIG. 1 is block diagram.

As shown in FIG. 1, in posterior lumbar interbody fusion (PLIF) in general, a spacer is inserted from the back of the spine. With this approach, a surgeon gains access to the spine by removing the bone (lamina) and retracting the nerves. Then the back of the disk can be removed and a spacer inserted. In other words, the weakened intervertebral disk is removed during a posterior lumbar interbody fusion and replaced with a cage or spacer.

Figure 2:
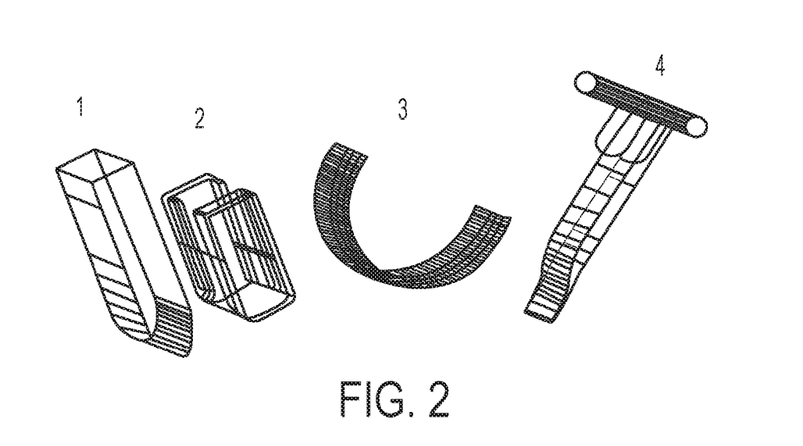
FIG. 2 is a block diagram of exemplary specially designed tools.

As shown in FIG. 2, the present invention includes use of certain specially designed tools. The tools include, for example, an access tube internal trochar 1, a slotted access tube 2, a curved track 3, a spatula muscle spreading instrument and footed tamp tool 4. Each of these specially designed tools are described more fully in conjunction with the subsequent text and figures. In addition, other materials are utilized, such as a cage implant.

In one embodiment, the cage implant has dimensions comparable to that of a direct lateral style cage, with depth ranges (A) from 16 mm to 20 mm, length ranges (B) from 35 mm to 60 mm, and height ranges (C) from 6 mm to 14 mm. The cage implant, in a specific embodiment, has interface recesses for connection with an inserter. The cage implant recesses are configured to permit capture and removal of the cage implant from a fully rotated position by using a recess which can accept a hook like retrieval device, and a recess with either screw threads or pincer grippable slots that can accept an introducer for impaction in a direction parallel to its main axis. Recesses with curved or square shapes, in the proximal end (tail), top side, or bottom side of the cage implant when viewed in the axial plane, in combinations necessary for achievement of these goals are envisioned. The purpose of these recesses are to permit first, a temporary docking of a removable inserter instrument onto the cage for the purpose of initial cage introduction into the interbody space, second, temporary docking of a tamp instrument onto the cage for the purpose of in situ rotation of the cage implant from a diagonal axis of insertion to a final position parallel to the floor, and third capture of the cage with a grabber or hook instrument in the event the cage were to become inadvertently malpositioned and require repositioning or removal.

Two embodiments of the inserter, with other possible variations, are described herein. In a first embodiment, an inserter with two separate connecting pieces that interface with the implant and can be angled independently with respect to the implant and tightened together at incremental points so as to hold the implant securely at a variety of different incrementally varying angles during positioning and initial implant introduction, and changeable to a perpendicular angle for force application to achieve subsequent rotation into final implant position.

In a second embodiment, the inserter is intended to engage the implant in a recess at its proximal (tail) end and is represented as two separate detachable symmetrical halves of the final inserter device, that are both sequentially inserted in an independent and modular fashion so as to minimize the size of the incision required for the insertion, and combined in situ to form the final complete instrument.

Additional tools for introducing the implant are described, for two variations of the implant introduction technique. A tapered slotted hollow passage tunnel is described, intended to be inserted through the skin and facsia to dock on the lumbar facet through an off-midline incision and enable visualization and operation on a small portion of the lumbar spine in a minimally invasive fashion, via internal serial passage of the dissection and disc prep instruments as well as the implant for installation into the interbody space by the surgeon down the visualization corridor provided by the tunnel. The taper in the tunnel distal end permits the tunnel to cut through the fascia without needing serial soft tissue dilation and requiring only a single removable internal trochar. The medially oriented slot enables an arc-shaped muscle sweeping tool to pass down the interior of the tunnel, after the implant's initial introduction into the interbody space, for the purpose of elevating muscle away from the medial portion of the visualized surgical field at the tunnel's end.

An arc shaped sweeping tool has a groove in its end and along its length, to interface with a second straight sweeping tool, which is designed to be inserted through a second symmetrically placed contralateral off-midline incision, which the surgeon performing a procedure of the type described herein would typically make for the purpose of implantation of percutaneous pedicle screw fixation hardware supplementing the interbody fusion. The purpose of the second sweeper is to hold the muscle in an elevated or retracted position during the introduction of a tamp instrument necessary to accomplish in situ rotation of the cage implant. The second sweeper, inserted through the contralateral incision and directed across the midline through the ipsilateral fascia, would interface with the groove on the end of the arc-shaped first sweeper. The purpose of this interface is to guide the second sweeper to the distal end of the visualization tunnel and help avoid inadvertent nerve injury which could result if the sweeper were to be aimed unknowingly at the exposed neural elements by the user.

A slotted tamp instrument, which may have either a footed or pegged distal working end to interface with a correspondingly configured accepting surface on the implant, as well as a groove along its length to interface with the second sweeper. For mini-open exposures, a self retaining retractor with a design modified from that of the minimal access tunnel is described, having a partially slotted convex-shaped outer (lateral) wall or blade, which provides the surgeon extra retraction of the tissue of during angling of the cage laterally and to maintain visualization of the proximal (tail) end of the cage during interface of a straight in-line introducer into the cage tail recess.

Figure 3:
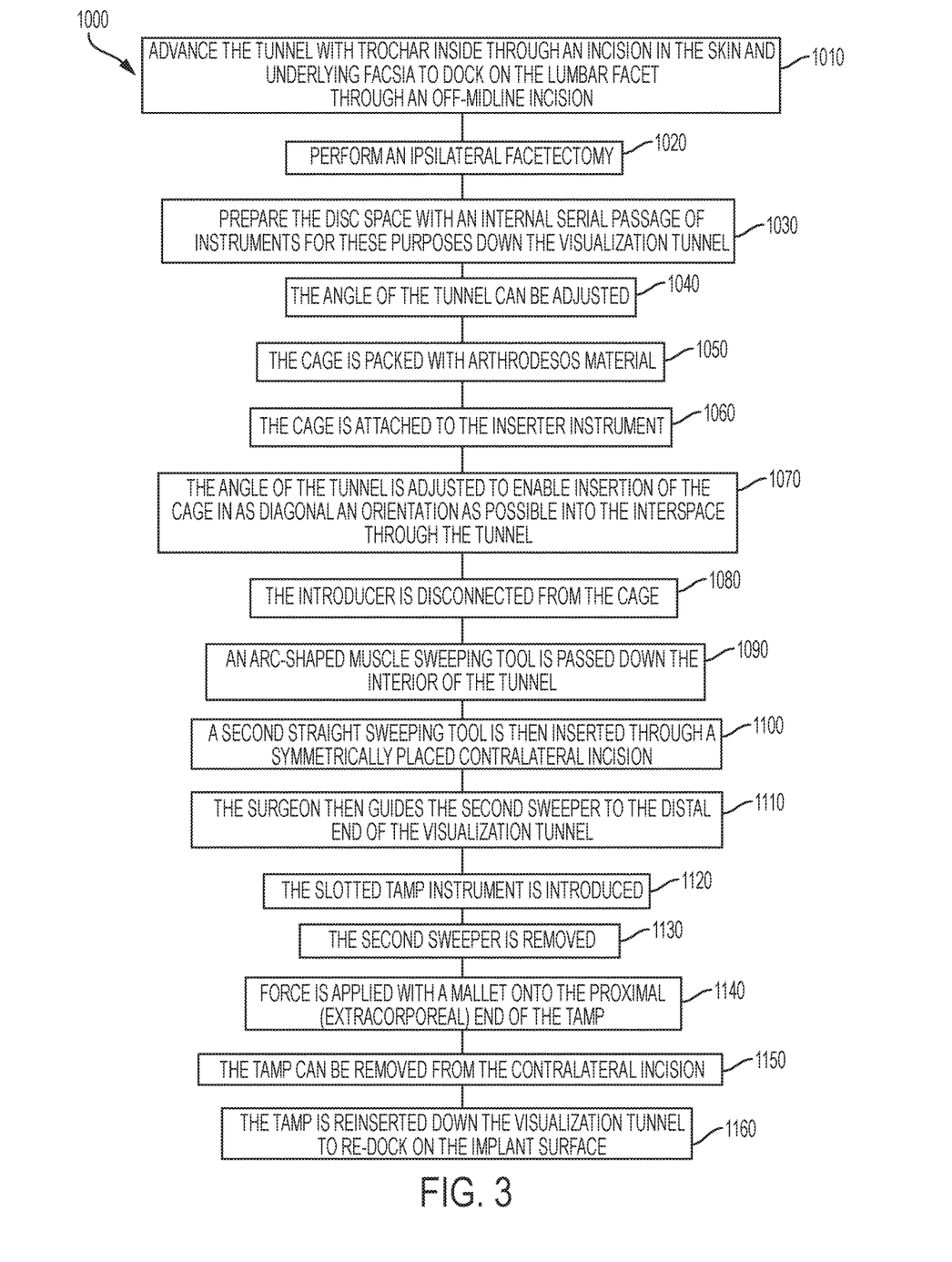
FIG. 3 is a flow diagram of a minimally invasive method.

As shown in FIG. 3, a minimally invasive method 1000 for the use of the implant for interbody fusion, including disc space and endplate preparation, includes advancing (1010) the tunnel with trochar inside through an incision in the skin and underlying facsia to dock on the lumbar facet through an off-midline incision. The method 1000 includes a surgeon performing (1020) an ipsilateral facetectomy and preparing (1030) of the disc space with an internal serial passage of instruments for these purposes down the visualization tunnel. The angle of the tunnel can be adjusted (1040) with respect to the operating table so as to accommodate separate sequential preparation of the contralateral pedicular zone portion of the endplates, with the tunnel oriented diagonally, and the ipsilateral pedicular zone portion of the endplates, with the tunnel oriented perpendicular to the floor. The cage is then packed (1050) with arthrodesos material, attached (1060) to the inserter instrument, and angle of the tunnel is adjusted (1070) to enable insertion of the cage in as diagonal an orientation as possible into the interspace through the tunnel. The introducer is disconnected (1080) from the cage. An arc-shaped muscle sweeping tool is passed down (1090) the interior of the tunnel, for the purpose of elevating muscle away from the medial portion of the visualized surgical field at the tunnel's end. A second straight sweeping tool is then inserted (1100) through a symmetrically placed contralateral incision, and interfaces with a groove on the end of the arc-shaped first sweeper. The surgeon then guides (1110) the second sweeper to the distal end of the visualization tunnel that helps avoid inadvertent nerve injury which could result if the sweeper were to be aimed unknowingly at the exposed neural elements. The slotted tamp instrument is then introduced (1120), guided by the second sweeper which slides into the groove on the tap outside the patient's body on the side contralateral to the facetectomy, and glides down the sweeper's length until its working end emerges into the surgical field, visualized by the user through the tunnel. The reason for the use of the contralateral incision for a tamp instrument is to permit the distal end of the tamp to interface with the correspondingly configured accepting surface on the implant in an angle as close as possible to perpendicular to the contacted surface of the implant during the initial application of the rotating impaction force. The second sweeper is removed (1130). Force is applied (1140) with a mallet onto the proximal (extracorporeal) end of the tamp, which serves to rotate the implant progressively toward a final position parallel to the floor. The tamp can be removed (1150) from the contralateral incision and reinserted (1160) down the visualization tunnel to re-dock on the implant surface once the implant's angle has been advanced sufficiently that use of the visualization tunnel for this purpose can accommodate an appropriately perpendicular angle of contact between the tamp and the implant.

FIGS. 4 through 8 illustrate the above process 1000.

Figure 4:
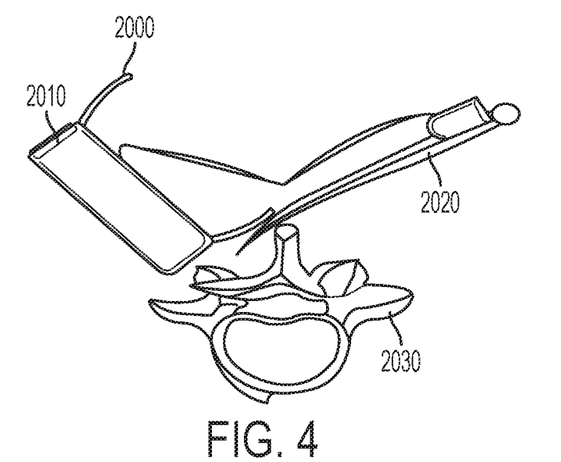
FIGS. 4-8 illustrate the process of FIG. 3.

FIG. 4 illustrates a curved track 2000 being introduced through a slotted wall access tube 2010 and used to guide the introduction of the muscle spreading spatula instrument 2020, inserted through a contralateral incision, over the bone 2030.

Figure 5:
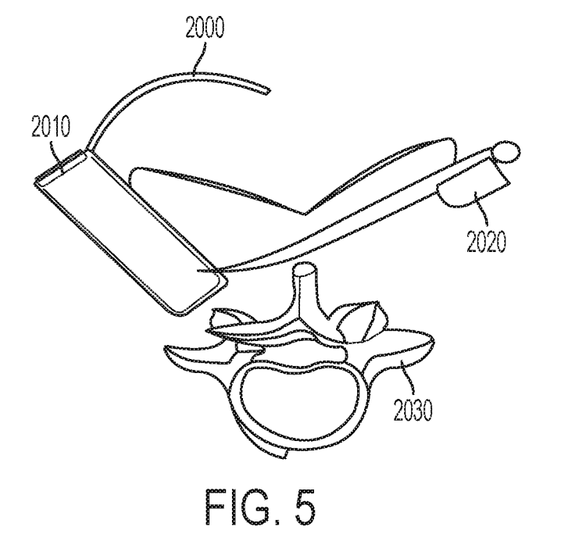

FIG. 5 illustrates a hand rotated muscle spreading spatula instrument 2020. This holds the muscle (not shown), which was elevated by the curved track 2000 and spatula tip, in an elevated position for the next step.

Figure 6:
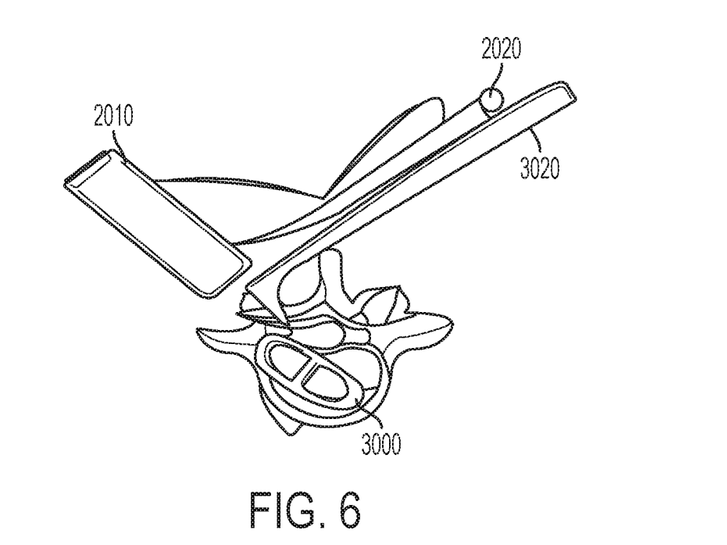

In FIG. 6, an interbody cage 3000 is introduced down the slotted wall access tube 2010. A footed rotator 3020 is slid along side the muscle spreading spatula instrument 2020 and its foot docked on a surface of the cage 3000. This holds the muscle (not shown), which was elevated by the curved track 2000 and spatula tip, in an elevated position for the next step.

Figure 7:
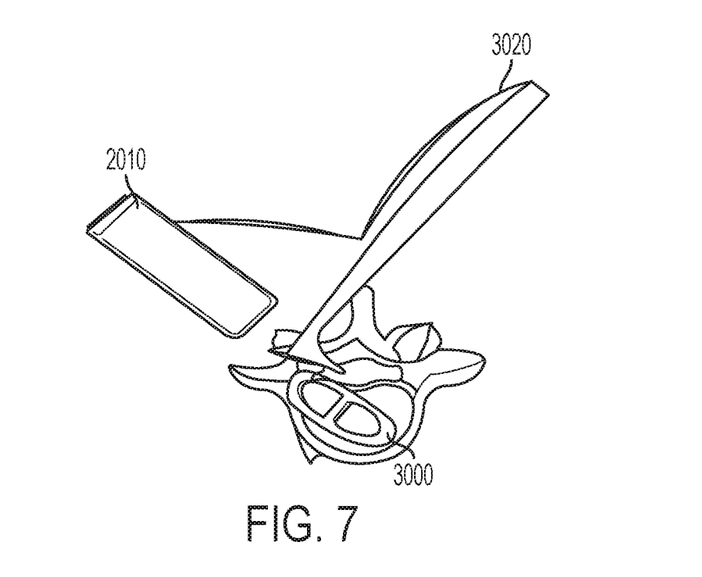

FIG. 7 illustrates how downward impaction applied on a footed tamp tool 3020 causes the cage 3000 to rotate.

Figure 8:
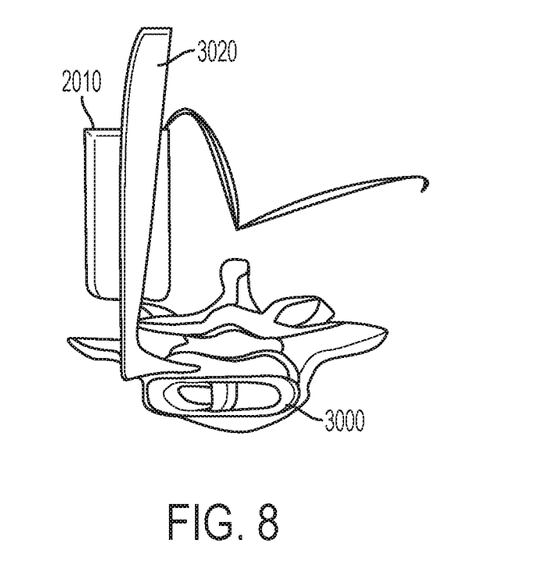

FIG. 8 illustrates how the footed tamp tool 3020 is withdrawn from the collateral incision and inserted down the slotted wall access tube 2010 to complete the rotation.

Figure 9:
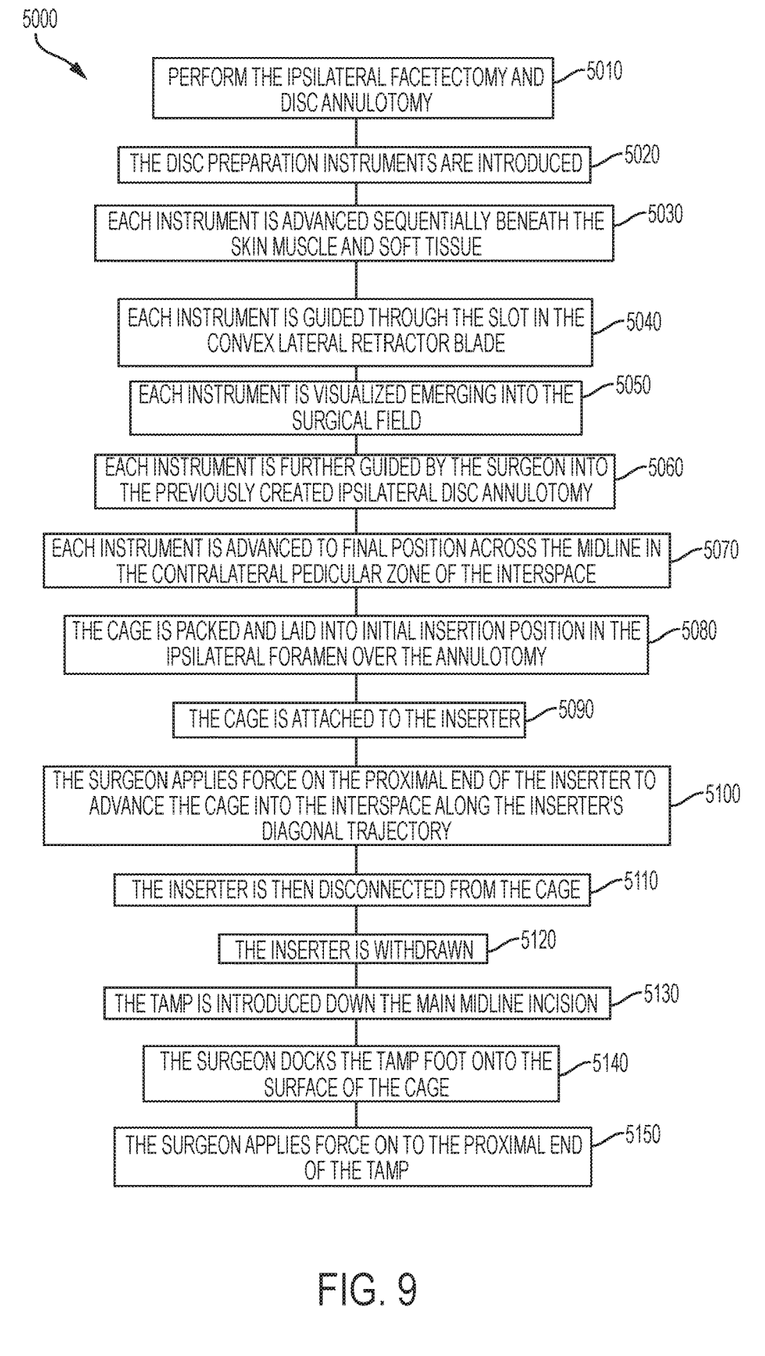
FIG. 9 is a flow diagram of a mini-open method.

As shown in FIG. 9, a mini-open method 5000 for the use of the implant for interbody fusion includes performing (5010) the ipsilateral facetectomy and disc annulotomy be performed using a standard midline incision technique with a self retaining retractor which has a slotted convex lateral blade. The disc preparation instruments are introduced (5020) by the surgeon into a separate stab incision, which is non-contiguous to the main incision, created in the skin about 12 to 14 cm off the midline. Each instrument is advanced (5030) sequentially beneath the skin muscle and soft tissue, guided (5040) through the slot in the convex lateral retractor blade, and visualized (5050) emerging into the surgical field where there it is further guided (5060) by the surgeon into the previously created ipsilateral disc annulotomy and advanced (5070) to final position across the midline in the contralateral pedicular zone of the interspace. A reason for this method for insertion of the disc prep instruments is to permit complete debridement of the contralateral pedicular zones of the endplates more sufficiently than could be achieved through a ipsilateral annulotomy from the midline incision. Following the disc preparation, the cage is packed (5080) and laid into initial insertion position in the ipsilateral foramen over the annulotomy, and attached (5090) to the inserter which is introduced from the stab incision through the slot in the lateral retractor blade as described above for the disc preparation instruments. The cage can be angled diagonally into the convex portion of the lateral retractor blade so as to achieve effective marriage with the inserter coming in from the stab incision. The surgeon applies (5100) force on the proximal end of the inserter to advance the cage into the interspace along the inserter's diagonal trajectory. The reason for this two-step marriage of the cage with the inserter, using the secondary stab incision, is to permit a more diagonal insertion angle than would be possible from the midline incision and to achieve a maximally contralateral position of the cage's distal tip (nose) after this step, all the while keeping the size of the secondary incision limited to that of a mere stab. The inserter is then disconnected (5110) from the cage and is withdrawn (5120), and the tamp is introduced (5130) down the main midline incision. The surgeon docks (5140) the tamp foot onto the surface of the cage and applies (5150) force on to the proximal end of the tamp, serving to rotate the cage to the final position parallel to the floor as described above.

FIGS. 10-15 illustrate the above process 5000.

Figure 10:
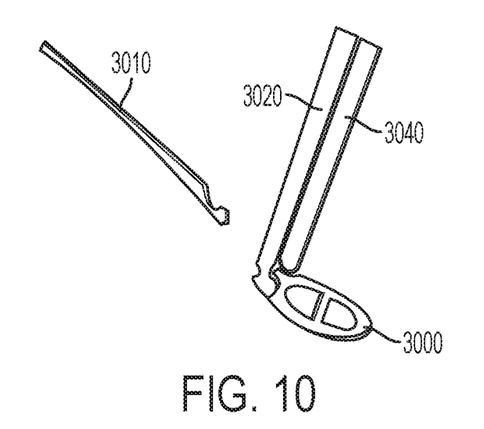
FIGS. 10-15 illustrate the process of FIG. 9.

FIG. 10 illustrates exemplary designs for an implant and attachments for downward and inward impaction.

Figure 11:
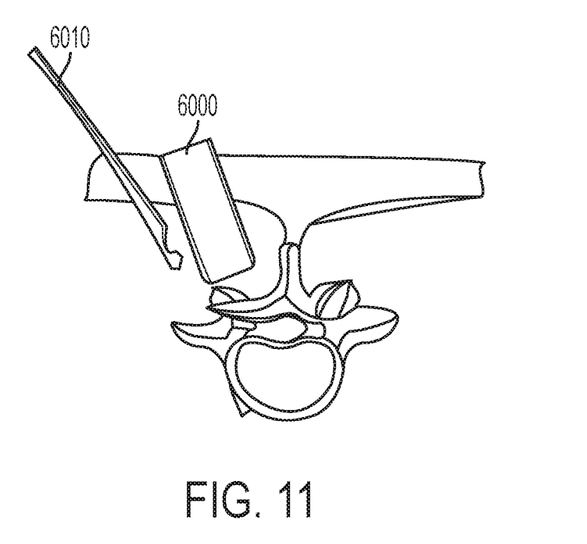

FIG. 11 illustrates a minimally invasive introduction of a large footprint interbody cage using a paramedian incision for a slotted access tube 6000 and a second, more lateral, stab incision, for insertion of a pole instrument 6010 for inward cage impaction.

Figure 12:
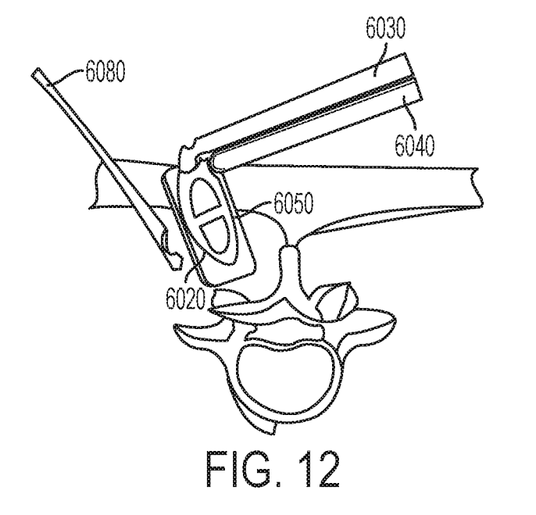

FIG. 12 illustrates how a cage 6020 with downward impaction attachments 6030, 6040 is introduced down a slotted access tube 6050.

Figure 13:
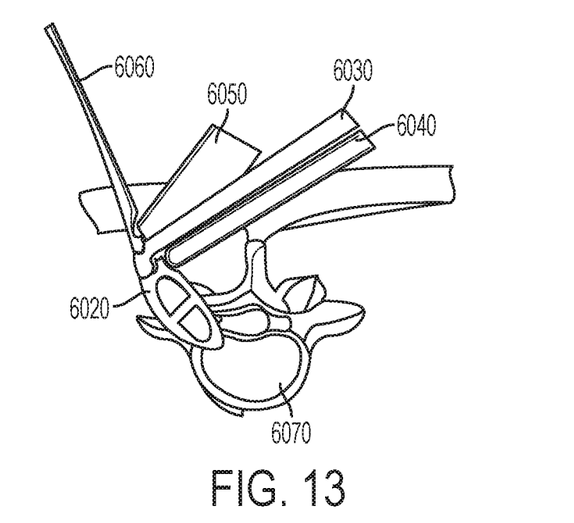

FIG. 13 illustrates how the slotted access tube 6050 is angled medially, and an inward impaction tool 6060 is docked onto the downward impaction attachment 6030 for initial advancement of the cage 6020 into an intervertebral space 6070.

Figure 14:
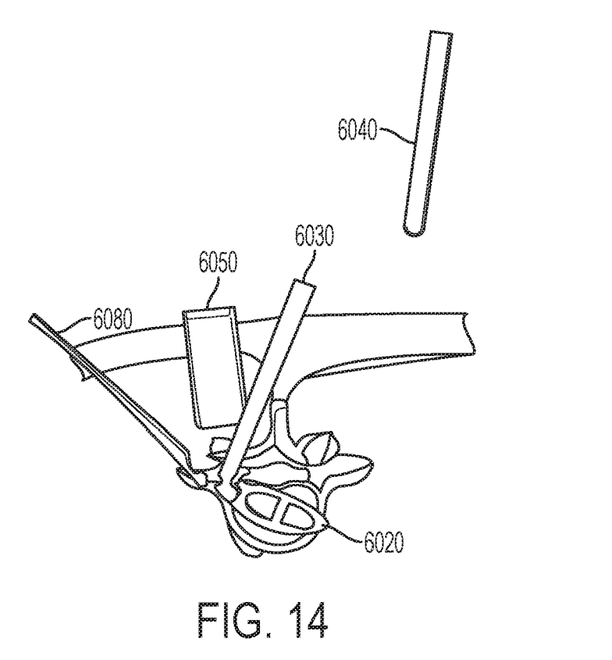

FIG. 14 illustrates how, with the inward downward impactor 6040 removed, the access tube 6050 and inward impaction pole 6080 are restored to their original angles as incremental impaction on the pole 6080 is performed.

Figure 15:
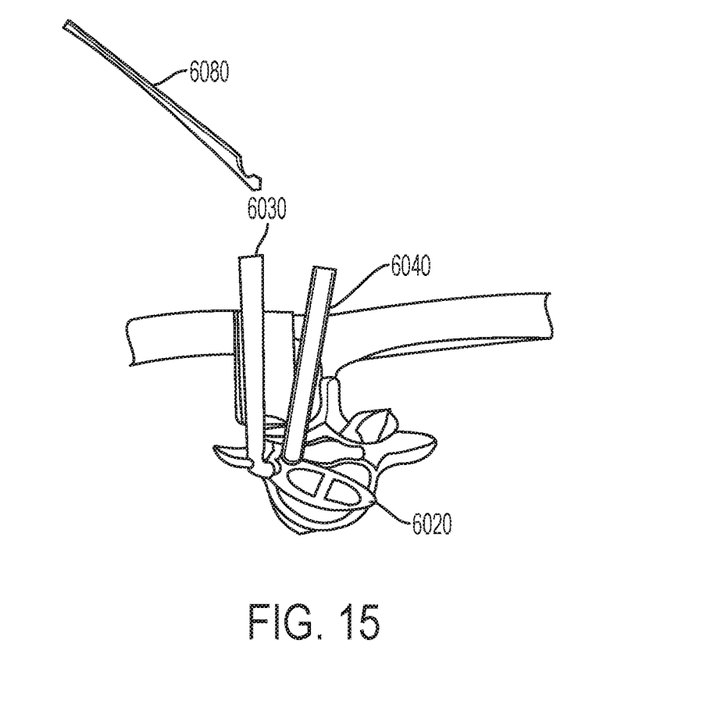

FIG. 15 illustrates how the pole 6080 is removed and both downward impaction attachments 6030, 6040 used to complete rotation of the cage 6020.

Figure 16:
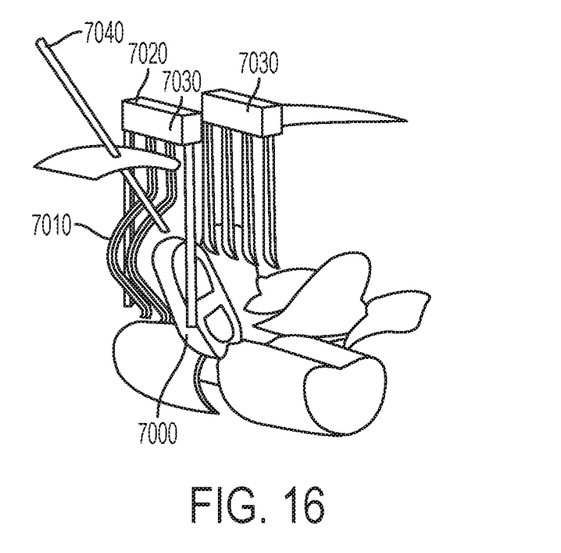
FIG. 16 is a block diagram of exemplary specially designed tools.

FIG. 16 illustrates some of the tools employed for the mini-open method 5000. The cage 7000 is laid into the cavity formed by the outwardly bent tines 7010 on the lateral blade 7020 of the two-bladed mini-open retractor 7030. The pole 7040 for impacting the cage 7000 into the interbody space is advanced through a stab incision separate from the main incision and attached to the cage 7000.

Figure 17:
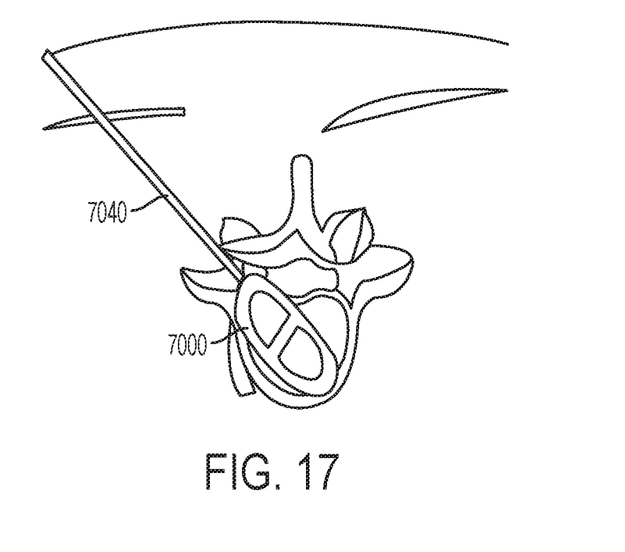
FIG. 17 is a block diagram.

As shown in FIG. 17, initial impaction on the pole 7040 through the separate lateral stab incision advances the cage 7000 into the interbody space in a diagonal trajectory.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A minimally invasive method for a use of an implant for interbody fusion, the method comprising:
    advancing a tunnel with a trochar inside through an incision in the skin and underlying facsia to dock on a lumbar facet through an off-midline incision and posterior approach;
    performing an ipsilateral facetectomy;
    preparing a disc space with an internal serial passage of instruments down a visualization tunnel through a posterior approach;
    adjusting an angle of the tunnel;
    packing a cage with arthrodesos material;
    attaching the cage to an inserter instrument;
    adjusting an angle of the tunnel to enable insertion of the cage through a posterior approach in as diagonal an orientation as possible into an interspace through the tunnel;
    disconnecting the introducer from the cage;
    passing an arc-shaped muscle sweeping tool down the interior of the tunnel;
    inserting a second straight sweeping tool through a symmetrically placed contralateral incision;
    guiding the second sweeper to a distal end of the visualization tunnel;
    introducing a slotted tamp instrument; and
    removing the second sweeper.

2. The method of claim 1 further comprising:
    applying a force with a mallet onto a proximal end of the tamp;
    removing the tamp from the contralateral incision; and reinserting the tamp down the visualization tunnel to re-dock on the implant surface.

* * * * *